United States Patent
Kawazu et al.

(10) Patent No.: US 6,563,024 B1
(45) Date of Patent: May 13, 2003

(54) PROCESS FOR TRANSFORMATION OF MATURE TREES OF EUCALYPTUS PLANTS

(75) Inventors: Tetsu Kawazu, Tsu (JP); Keigo Doi, Kameyama (JP); Keiko Kondo, Kameyama (JP)

(73) Assignee: OJI Paper Co., Ltd., Tokyo (JP)

( * ) Notice: Subject to any disclaimer, the term of this patent is extended or adjusted under 35 U.S.C. 154(b) by 0 days.

(21) Appl. No.: 09/564,811

(22) Filed: May 5, 2000

(30) Foreign Application Priority Data

May 7, 1999 (JP) .......................................... 11-127025

(51) Int. Cl.[7] .................. C12N 15/00; C12N 15/04; C12N 15/84; A01H 4/00; A01H 5/00
(52) U.S. Cl. ................... 800/294; 800/298; 435/419; 435/430.1; 435/469
(58) Field of Search .................. 800/294, 298; 435/469, 410, 419, 420, 430.1

(56) References Cited

U.S. PATENT DOCUMENTS 4,672,035 A * 6/1987 Davidonis et al. .......... 435/240

FOREIGN PATENT DOCUMENTS

| GB | 2 195 656 A | 4/1988 |
|---|---|---|
| GB | 2 211 204 A | 6/1989 |
| JP | 62-55020 | 3/1987 |
| JP | 63-7720 | 1/1988 |
| JP | 2-265419 | 10/1990 |
| JP | 4-4828 | 1/1992 |
| JP | 7-203790 | 8/1995 |
| JP | 8-89113 | 4/1996 |
| JP | 9-98684 | 4/1997 |
| JP | 10-304785 | 11/1998 |
| WO | WO 96/25504 | 8/1996 |
| WO | WO 97/23126 | 7/1997 |
| WO | WO 97/25434 | 7/1997 |
| WO | WO 98/13503 | 4/1998 |
| WO | WO 98/56932 | 12/1998 |
| WO | WO 00/15813 | 3/2000 |

OTHER PUBLICATIONS

Teulieres et al, "Progress Towards Genetics Transformation of Eucalyptus Species", 1997, Biol. Science Symposium, pp 75–78.*
XP–002185331; Biosciences Information Service, 1998; Online Database, abstract.
XP–002185330; Biosciences Information Service, 1996; Online Database, abstract.
XP–002185332; Biosciences Information Service, 1995; Online Database, abstract.
XP–002185333; Biosciences Information Service, 1990; Online Database, abstract.
XP–002185334; Biosciences Information Service, 1987; Online Database, abstract.
XP–002185351; Biosciences Information Service, 1996; Online Database, abstract.

* cited by examiner

*Primary Examiner*—Elizabeth F. McElwain
*Assistant Examiner*—Cynthia Collins
(74) *Attorney, Agent, or Firm*—Armstrong, Westerman & Hattori, LLP

(57) ABSTRACT

The present invention discloses a process for transforming mature trees of Eucalyptus plants comprising: induction adventitious shoots from segments of the explant obtained from an adult tree of a Eucalyptus plant, preculturing the adventitious shoots in infection induction medium, infecting the adventitious shoots subjected to infection induction treatment with infection medium containing Agrobacterium tumefaciens, and rotary-culturing the infected explant segments in sterilization medium containing antibiotic; whereby sterilizing and forming transgenic calli, which regenerate transgenic plants by way of formation of shoot primordia by rotary-culturing under illumination.

5 Claims, No Drawings

PROCESS FOR TRANSFORMATION OF MATURE TREES OF EUCALYPTUS PLANTS

BACKGROUND OF INVENTION

1. Field of the Invention

The present invention relates to a process for creating transgenic Eucalyptus plants comprising infecting adventitious shoots derived from mature trees of Eucalyptus plants with Agrobacterium tumefaciens.

2. Related Art

Eucalyptus plants are polygenus plants comprising more than 500 species that are native to the Oceania region and predominantly Australia. Many of these Eucalyptus plants have excellent growth properties, the ability to adapt to various environments, and a low level of serious insect damage. Since they are also suited industrially to the production of lumber, pulp and firewood, afforestation of Eucalyptus species plants is conducted in various regions around the world. According to a survey conducted by The United Nations Food and Agriculture Organization (FAO) in 1990, Eucalyptus plants are planted over an estimated area of 10 million hectares throughout the world, accounting for approximately one-fourth of the artificial forest area in tropical regions. In order to further enhance the productivity of these Eucalyptus plants, breeding is conducted by selection and hybridization. In Brazil, for example, breeding has been performed by selection and hybridization targeting to enhancement of basic density and pulp yield, which are two important factors in the paper pulp industry, in addition to growth properties, and yield has been reported to be increased by 2.3 times in terms of the basic density and by 2.4 times in terms of the pulp yield.

Moreover, in recent years, specific gene isolation, modification and reinsertion of recombinant genes into plants has become possible in numerous plant species due to the progress of gene manipulation technology, and plant breeding is being aggressively conducted involving transformation of useful genes isolated from heterogeneous organisms or modified genes of genes inherently retained by the plant itself, which was not possible with conventional breeding methods such as selection and hybridization breeding. Numerous examples of such breeding are reported in the literature, including breeding of loblolly pine (Sederoff, et al., Bio/Technology 4: 647–649 (1986)), poplar (Fillatti et al., Mol. Gen. Genet. 206: 192–199 (1987)), walnut (McGranahan, et al., Bio/Technology 6: 800–804 (1988)), apple (James, et al., Plant Cell Rep. 7; 658–661 ) (1989)) and plum (Mante, et al., Bio/Technology 9: 853–857 (1991)).

However, not all woody plants are able to be transformed with stability at the present time. In order to establish transformation technology using Agrobacterium tumefaciens in the target woody plant, it is necessary to develop (1) a method for regenerating the plants from a transformed cell, and (2) a method for infecting Agrobacterium tumefaciens into the plant tissue. In order to accomplish this, the inventors of the present invention have developed methods of regenerating plants from tissue or isolated cells of Eucalyptus plants by the utilization of shoot primordia (Japanese Unexamined Patent Publications Nos. 62-55020, 63-7720, 64-47318, 2-265419, 4-4828, 5-236832, 9-98684, UK Patent No. GB2195656B; U.S. Pat. No. 5,310,673), the utilization of protoplasts (Japanese Unexamined Patent Publications Nos. 2-128631, 64-43138, 2-128631, UK Patent No. GB2231585B; U.S. Pat. No. 5,310,673), and the utilization of precocious branches (Japanese Unexamined Patent Publication No. 10-304785). Moreover, the inventors of the present invention have proposed a method of producing transgenic plants comprising introducing a foreign gene by electroporation into the protoplast of a Eucalyptus plant aiming the transformation using these regeneration methods (Japanese Unexamined Patent Publication No. 4-53429).

However, in the case of producing transformants by electroporation, not only is considerably time required until a transformant is obtained, but there is also the problem of transformants being obtained at a low frequency. Therefore, a method was proposed for efficiently obtaining transgenic plants by infecting the cotyledon or hypocotyl derived from seedlings of Eucalyptus plants with Agrobacterium tumefaciens (Japanese Unexamined Patent Publications Nos. 7-203790 and 8-89113).

These methods made it possible to transform Eucalyptus plants for which transformation was previously difficult. However, in the case of infecting segments of the explant from mature trees growing outdoors with Agrobacterium tumefaciens using the same methods, problems occurred that included blackening of segments of the explant by polyphenol induced as a result of wounding or co-culturing with Agrobacterium tumefaciens, thereby preventing the production of transgenic plants.

On the other hand, with respect to transformation of Eucalyptus plants with Agrobacterium bacteria by persons other than the inventors of the present invention, although the successful gene insertion has been previously reported in *Eucalyptus globulus,* regeneration of the transgenic plant was not performed (Landre, et al., Plant Sci. 127: 81–91 (1997); Serrano, et al., J. Exp. Botany 47: 285–290 (1996)). In addition, although successful regeneration of the transgenic plant has been reported in *Eucalyptus camaldulensis,* due to the low transformation efficiency, this did not lead to a stable transformation system, (Mullins, et al., Plant Cell Rep. 16: 787–791 (1997)). Moreover, although it has also been reported again in *Eucalyptus camaldulensis* that a transgenic plant was successfully regenerated using the hypocotyl for the transgenic material, since the hypocotyl is used for the transformation material, transformation is not possible for a specific mature tree (Ho, et al., Plant Cell Rep. 17: 675–680 (1998)). Moreover, a method is proposed in International Application WO96/25504 for the purpose of transforming mature trees in which segments of the explant are removed from a mature tree of a Eucalyptus plant followed by tissue culturing and transformation to the resulting plant.

DISCLOSURE OF INVENTION

Although the prior experiments enabled the transformation of a mature tree of a eucalyptus plant, the formation rate of transgenic calli and the regeneration rate of transgenic plants were inadequate.

As a result of various studies to solve the above problems, the inventors of the present invention found that mature tree of Eucalyptus plants can be efficiently transformed by inducing tissue cultures having high transformation ability from mature trees of Eucalyptus plants.

Accordingly, the present invention provides a process for producing transgenic plants by inducing adventitious shoots that can be efficiently transformed from a mature tree of Eucalyptus plant, infecting the adventitious shoots with Agrobacterium tumefaciens, forming transgenic calli from the infected adventitious shoot, forming shoot primordia from the transgenic calli and regenerating transgenic plants from the shoot primordia.

More specifically the present invention provides a process for production of transgenic Eucalyptus plants from a mature tree of Eucalyptus plant, comprising the steps of:

(1) preparing a shoot tip explant from a mature tree of Eucalyptus plant;

(2) inducing the shoot tip explant to form adventitious shoots;

(3) pre-culturing the adventitious shoots to prepare infection in an infection induction medium;

(4) infecting segments of explant cut out from the pre-cultured adventitious shoots with Agrobacterium tumefaciens in an infection medium;

(5) rotary-culturing the segments of the explant from the step (4) in a medium for sterilization containing antibiotics so as to sterilize the Agrobacterium tumefaciens attached to the segments of the explant, to form calli and to select transformed calli;

(6) forming shoot primordia from the transformed calli; and (7) regenerating transgenic plants from the transformed calli.

In preferred embodiments, the adventitious shoots infected by Agrobacterium tumefaciens are precocious branches or axillary shoots, and preferably precocious branches.

In a preferred embodiment, the infection in the step (4) is carried out by infecting the adventitious shoots with Agrobacterium tumefaciens after pre-culturing in the step (3) in an infection induction medium containing 0.01 to 2 mg/l of naphthaleneacetic acid (NAA) for 7 to 21 days under dark conditions.

According to a preferred embodiment of the present invention, the infection medium used in the step (4) contains 0.2 to 5.0 mg/l of naphthaleneacetic acid (NAA) and 0.02 to 1.0 mg/l of 1-(2-chloro-4-pyridyl)-3-phenylurea or N-(2-chloro-4-pyridyl)-N'-phenylurea (4-PU or 4CPUU).

According to a preferred embodiment of the present invention, the eucalyptus plant is *Eucalyptus camaldulensis, Eucalyptus globulus, Eucalyptus grandis, Eucalyptus urophylla,* or a hybrid derived from one of them as maternal or paternal tree.

DETAILED DESCRIPTION

The following provides a detailed explanation of the process for efficient transformation of mature trees of Eucalyptus plants according to the present invention.

The transformation method of the present invention allows the production of transgenic plants by using as materials for infection by Agrobacterium tumefaciens (1) precocious branches formed from a shoot tip explant aseptically excised from a mature tree of a Eucalyptus plant by rotary-culturing the shoot tip explant under illumination in an artificial liquid medium containing inorganic salts, carbon sources and vitamins, in accordance with a previously proposed mass propagation technique for woody plants (Japanese Unexamined Patent Publication No. 10-304785), or by using (2) axillary shoots obtained by aseptically excising a shoot tip explant from a mature tree of a Eucalyptus plant and planting the shoot tip explant in an artificial medium containing inorganic salts, carbon sources, vitamins and plant growth hormones. Moreover, mature trees of Eucalyptus plants can be efficiently transformed by (1) selecting the hormone conditions used for the Agrobacterium infection medium, and/or (2) pre-culturing precocious branches or axillary shoots by transplanting them to an artificial medium containing inorganic salts, carbon sources, vitamins and plant growth hormones for induction of infection prior to infection and culturing under dark conditions.

Preparation of Precocious Branches from Mature Trees for Infecting with Agrobacterium tumefaciens An explant measuring 5 to 20 mm that contains a shoot apex or axillary bud is prepared from a fresh branch of a mature tree of Eucalyptus plant grown outdoors and sterilized using ordinary sterilization methods, and rotary-cultured in a liquid medium, such as WPM (Loyd & MCCown, Proc. Int. Plant Prop. Soc. 30: 421–427 ) 1980)), B5 (Gamborg's B5 medium) (Gamborg, et al., Exp. Cell Res. 50: 151–158 (1968)), MS (Murashige and Skoog medium) (Murashige & Skoog, Physiol. Plant 15: 473–479 (1962)) or other basal media, supplemented with, for example, 1 to 3% sucrose as the carbon source. Culturing conditions are a rotating speed of 1 to 10 rpm, illumination intensity of 1,000 to 2,000 lux at the lower limit and 10,000 to 20,000 lux at the upper limit, and temperature of 15 to 35° C. As a result of rotary-culturing under these conditions in 30 to 50 days, precocious branches are obtained that simultaneously demonstrate elongation of shoots and micropropagation. Furthermore, micropropagation can be carried out repeatedly by subculturing shoot tip segments containing shoot apices of the resulting precious branches.

Preparation of Axillary Shoots from Mature Trees for Infecting with Agrobacterium tumefaciens An explant measuring 5 to 20 mm that contains shoot apex or axillary bud is prepared from a fresh branch of a mature tree of Eucalyptus plants grown outdoors sterilized using ordinary sterilization methods, and planted in an axillary shoot induction medium containing 0.01 to 0.02 mg/l of plant growth hormones as auxins such as naphthaleneacetic acid (NAA), indole-3-butyric acid (IBA) or indole-3-acetic acid (IAA); 0.01 to 0.02 mg/l of cytokinins such as 6-benzyladenine (BA), 1-(2-chloro-4-pyridyl)-3-phenyl urea (4-PU), N-(2-chloro-4-pyridyl)-N'-phenyl urea (4CPPU) or 1-phenyl-3-(1,2,3-thiadiazol-5-yl) urea (TDZ); 1 to 3% of a carbon source such as sucrose; and gelling agents such as 0.03 to 0.6% agar or 0.15 to 0.3% gellan gum in, for example, WPM, B5or MS basal medium.

Examples of culturing conditions include illumination intensity of 1,000 to 10,000 lux and temperature of 15 to 35° C. Axillary shoots can be obtained by culturing for 20 to 50 days under the above conditions. Furthermore, the resulting axillary shoots can be micropropagated repeatedly by subculturing shoot tip segments containing shoot apices cut from the axillary shoot.

Infection Induction Treatment of Adventitious Shoots

Segments in length of 20–50 mm containing the shoot apices are cut off from the precocious branches or axillary shoots with a knife, and then planted in an infection induction medium containing 0.01 to 0.02 mg/l of auxins such as NAA, IBA or IAA; 0.01 to 0.2 mg/l of cytokinins such as BA, 4-PU, 4CPPU or TDZ; 1 to 3% of a carbon source such as sucrose; and a gelling agent such as 0.3 to 0.6% agar or 0.15 to 0.3% gellan gum, in a basal medium, for example, WPM, B5 or MS. Culturing was performed under dark conditions for 7 to 20 days at a temperature of 15 to 35° C.

Preparation of Agrobacterium tumefaciens

A strain of Agrobacterium tumefaciens is prepared in which its Ti plasmid has been disarmed or not disarmed.

After modifying a gene to be inserted so as to be expressed in plant cells, it is joined to a Ti plasmid vector or binary vector and the vector is used to transform Agrobacterium tumefaciens (Chilton, et al., Proc. Natl. Acad. Sci. USA 77: 4060–4064 (1980)), (Herrera-Estralla, et al., Nature 303: 209–213 (1983)), Agrobacterium tumefaciens obtained with the above method is cultured in an L-broth (Miller Experiments in Molecular Genetics (1972), 10 g/l of Bact-tryptone, 5 g/l of Bact-yeast extract and 5 g/l of NaCl) supplemented with a proper amount of selection antibiotic defined by the antibiotic resistance gene retained by the vector, overnight until the culture's O.D. 600 reaches 0.8 or more.

Infection with Agrobacterium tumefaciens

After washing the plant tissues of the precocious shoots or axillary shoots subjected to infection induction treatment, with 0.1% Tween-20, the plant tissues are cut with a knife to lengths of 2to 10 mm and planted in an Agrobacterium infection medium, for example, a liquid medium such as WPM, B5 or MS basal medium supplemented with cytokinins such as 4-PU, 4CPPU, BA, TDZ or kinetin; and auxins such as NAA, 2,4-D or IAA, sugar such as sucrose, and galactose, and acetosyringone, and inoculated with Agrobacterium tumefaciens. More preferably, after immersing the explant segments in an Agrobacterium culture broth, they are embedded in solid medium containing the above components except Agrobacterium tumefaciens. This is then stationary cultured for 1 to 2 days under dark conditions at a temperature of 20 to 30° C. to infect with Agrobacterium tumefaciens.

Sterilization of Agrobacterium tumefaciens

Explant segments infected with Agrobacterium tumefaciens as described above are planted in a sterilization medium, for example, liquid medium such as WPM, B5 or MS basal medium, supplemented with cytokinins such as 4-PU, 4CPPU, BA, TDZ or kinetin; and auxins such as NAA, 2,4-D or IAA; antibiotics for sterilizing Agrobacterium tumefaciens such as carbenicillin, vancomycin or cefotaxime sodium; and sugar. The infected explant segments are then rotary-cultured for 3 to 14 days under illumination of 0 to 2,000 lux and at a temperature of 15 to 35° C. to sterilize the Agrobacterium tumefaciens.

Formation of Transgenic Shoot Primordia

Explant segments completely sterilized of Agrobacterium tumefaciens are rotary-cultured in a liquid medium such as WPM, B5 or MS basal medium supplemented with, plant growth hormones cytokinins such as 4-PU, 4CPPU, BZ, TDZ or kinetin, and auxins such as NAA, 2,4-D or IAA, carbon source, antibiotics for sterilizing Agrobacterium tumefaciens, and antibiotics for selecting transformed calli. Culture conditions are a rotating speed of 1 to 10 rpm, illumination intensity of 0 to 20,000 lux and temperature of 15 to 35° C. When culturing is continued by subculturing to fresh media at an interval of 14 to 40 days, the formation of whitish-yellow transformed calli are observed on the explant segments at 20 to 30 days after the start of the culturing. The resulting calli are cut from the explant segments with a knife and rotary-cultured under illumination to allow the induction of transgenic shoot primordia at 40 to 120 days from the start of the culturing.

Regeneration of Transgenic Plants

Transgenic shoot primordia obtained by the rotary-culturing as described above are cultured in a medium for regenerating shoots, for example a seedling medium B5 or MS basal medium, supplemented with plant growth hormones auxins such as NAA, 2,4-D and IAA, and cytokinins such as BA, 4-PU, 4CPPU, kinetic, zeatin or TDZ; carbon source; agar or gellan gum; and antibiotic for selecting transformed calli. Culturing is performed for about 60 days at a temperature of 15 to 35° C. and illumination intensity of 2,000 to 3,000 lux to regenerate the shoots, followed by rooting of individual shoots to obtain complete transgenic plants.

EXAMPLES

Although the following provides a more detailed explanation of the present invention based on its examples, the present invention is not limited to these examples.

Example 1

Test Plants

*Eucalyptus camaldulensis* was used.

Preparation of Precocious Branches

After sterilizing a plant tissue containing shoot apices cut from a five-year old *Eucalyptus camaldulensis* grown outdoors, for 30 seconds with 70% ethanol and for 1 minute with 10-fold diluted sodium hypochlorite solution, the plant tissue was washed three times with sterilized water followed by aseptically cutting the explant segments containing shoot apices using forceps and a knife. The resulting explant segments containing shoot apices were transplanted to a liquid medium containing 1% sucrose in B5 basal medium, followed by induction of precocious branches by vertical-rotary-culturing, that were used as the experiment materials.

Infection Induction Treatment of Precocious Branches

Explant tissues of 20 to 25 mm length containing shoot apices were cut from the precocious branches demonstrating stable growth with a knife, and planted in an infection induction medium containing 0.02 mg/l NAA, 1% sucrose and 0.02% gellan gum in B5 basal medium. Culturing was performed for 7 to 14 days at a temperature of 26 to 28° C. under dark conditions.

Preparation of Agrobacterium tumefaciens

Agrobacterium tumefaciens strain EHA101, in which Ti plasmid has been disarmed, (Hood, et al., J. Bacteriology 168: 1291–1301 (1986)) was used. Regardless of what gene is used to be inserted, that gene can be expressed by substituting its promoter with a plant promoter. Here, binary vector pIG121-Hm (Nakamura, et al., Plant Biotechnology II, pp. 123–132, Modern Chemistry Supplement (1991)), which has a hygromycin resistance gene and kanamycin resistance gene as selection marker genes and β-glucuronidase (intron GUS) gene contains the first intron of the catalase gene of castor oil plant as reporter gene, in the T-DNA region was used to transform Agrobacterium tumefaciens. Agrobacterium tumefaciens strain EHA101/pIG121-Hm retaining the above intron GUS gene was prepared by culturing overnight at 30° C. in L-broth containing kanamycin at a concentration of 50 mg/l and hygromycin at a concentration of 50 mg/l.

Infection of Eucalyptus Plant Tissue with Agrobacterium

After cutting the precocious branches subjected to the infection induction treatment to segments of 2 to 10 mm length with a knife, the segments were immersed in the culture medium of Agrobacterium tumefaciens strain EHA101/pIG121-Hm prepared according to the method described above. After wiping off the culture medium adhered to the segments of the precocious branches with filter paper, the sections of the precocious branches were embedded in an infection medium containing 2 mg/l NAA, 0.2 mg/l 4-PU, 1 mM galactose, 10 μM acetosyringone, 3% sucrose and 0.02% gellan gum in B5 basal medium, followed by stationary-culturing for 2 days at a temperature of 26° C. and under dark conditions to infect the precocious branches with Agrobacterium tumefaciens.

Sterilization of Agrobacterium

The explant segments treated as described above were transplanted to a sterilization medium containing 2 mg/l NAA, 0.2 mg/l 4-PU or 4CPPU, 3% sucrose, and 500 mg/l of carbenicillin as antibiotic for sterilizing Agrobacterium attached to the explant segments, and were vertical-rotary-cultured for 7 - days at a temperature of 26° C. and rotating speed of 2 rpm under dark conditions to sterilize the Agrobacterium tumefaciens.

Formation of Transgenic Shoot Primordia

Explant segments completely sterilized of Agrobacterium tumefaciens were planted at the rate of 5 segments per test tube in a liquid medium containing 0.02 mg/l NAA, 0.2 mg/l 4-PU, 3% sucrose and 10 mg/l hygromycin in B5 basal medium. As a result of vertical-rotary-culturing at a rotating speed of 2 rpm and temperature of 26° C. for 7 days under dark conditions and then for 1 month under illumination at a illumination intensity of 2,000 lux at the lower limit and 20,000 lux at the upper limit, the formation of transgenic calli that were yellowish-white and measured 2 to 3 mm was observed on the explant segments. Culturing of the resulting calli was continued by subculturing into a fresh medium at intervals of 14 to 40 days. Transgenic shoot primordia were obtained at 40 to 120 days from the start of vertical-rotary-culturing under illumination.

Regeneration of Transgenic Plants

Shoot primordia cut into squares measuring about 5 mm on a side were transplanted to a seedling medium containing 0.02 mg/l NAA, 0.2 mg/l BA, 1% sucrose, 0.2% gellan gum and 10 mg/l hygromycin in B5 basal medium to regenerate transgenic shoots from the transgenic shoot primordia obtained by rotary culturing. As a result of culturing for 16 hours under illumination at 25° C. and illumination intensity of 4,000 lux, shoot regeneration was observed 1 month after the start of the culturing. By transplanting the resulting shoots in a rooting medium containing 0.01 mg/l NAA, 1% sucrose, 0.35% agar in 10 mg/l hygromycin in B5 basal medium, complete plants were grown, wherein rooting was observed after 1 month. Namely, in the case of this method, 5 to 12 months were required to produce transgenic plants from the time of infection to explant segments.

Confirmation of Presence of Transgene in Transgenic Plants

When the presence of the transgene was confirmed by PCR for four plants obtained by antibiotic selection, the transgene was confirmed to be present in all four plants. On the basis of this examination, this method was verified to be effective for transformation of Eucalyptus plants.

Confirmation of Expression of Transgene in Transgenic Plants

When expression of intron GUS gene was investigated by tissue staining (Kosugi, et al., Plant Science 70: 133–140 (1990)) for the plants confirmed to contain the transgene by PCR, potent expression of intron GUS gene was confirmed around the leaves and in the root tips and root hairs.

Example 2

Plant tissue containing the shoot apices cut from a five-year-old Eucalyptus camaldulensis grown outdoors was sterilized in the same manner as described in Example 1,after which the sterilized tissue containing shoot apices was cut out. The resulting plant tissue containing shoot apices were planted into a solid medium supplemented with NAA at a concentration of 0.02 mg/l and BA at a concentration of 0.02 mg/l, and containing 1% sucrose and 0.2% gellan gum in B5 basal medium, followed by culturing for 30 days under conditions of illumination density of 5,000 lux and temperature of 26° C. to obtain axillary shoots. After infecting the resulting axillary shoots with Agrobacterium tumefaciens strain EHA101/pIG121-Hm using the same infection medium as described in Example 1, selection of transgenic calli was performed according to the same method as described in Example 1. The resulting transgenic calli were able to regenerate transgenic plants according to the same method as described in Example 1, and expression of inserted intron GUS gene was detected.

Comparative Example 1

Precocious branches and axillary shoots were induced from 30 *Eucalyptus camaldulensis* plants grown independently outdoors. After infecting the mature leaves of 16 plants sampled outdoors with Agrobacterium tumefaciens using the same method as described in as Example 1, the number of transgenic calli that expressed intron GUS gene was measured 30 days later. As a result, the formation of transgenic calli was observed in 56.7% of the precocious branches, while in 6.7% of the axillary shoots. On the other hand, it was observed at 0% in the mature leaves. In addition, in the case of using the mature leaves as materials for infection, browning of the leaf color or growth of non-transgenic cells tended to occur due to co-culturing with Agrobacterium tumefaciens, thus clearly demonstrating that it is difficult to obtain transgenic calli.

Comparative Example 2

With the exception of inducing precocious branches from three *Eucalyptus camaldulensis* plants, and performing infection induction treatment with the concentration of NAA in the precocious branch infection induction medium at 0, 0.02, 0.2 or 2.0 mg/l, the precocious branches were infected with Agrobacterium tumefaciens strain EHA101/pIG121-Hm in the same manner as described in Example 1, and the number of transgenic calli that express intron GUS gene was investigated 30 days after the start of the infection induction treatment. Those results are shown in Table 1. For plant 1, the case of testing precocious branches of the untreated group on which infection treatment was not performed, transformation efficiency of 23.1% was obtained. In contrast, in the experimental group in which infection induction treatment was performed at an NAA concentration of 0.02 mg/l, transgenic calli were observed in 72.9% of the precocious branches tested. In addition, in the untreated group of plant 2 as well in which infection was difficult, transgenic calli were observed following infection induction by NAA. One the basis of these findings, infection induction treatment of precocious branches was clearly shown to be effective in improving transformation efficiency.

TABLE 1

| Plant No. | Untreated group | Infection induction group (NAA) mg/l | | | |
|---|---|---|---|---|---|
| | | 0 | 0.02 | 0.2 | 2.0 |
| 1 | 6/26 (23) | 65/109 (60) | 70/96 (73) | 48/75 (64) | 44/89 (49) |
| 2 | 0/6 (0) | 0/11 (0) | 1/13 (8) | 5/16 (31) | 3/16 (19) |
| 3 | 2/17 (12) | 31/51 (61) | 24/35 (69) | 16/42 (38) | 24/40 (59) |

No. of transgenic calli/No. of tested segments
( ): Transformation efficiency = No. of transgenic calli/No. of tested segments × 100 (%)

Example 3

With the exception of inducing precocious branches from a different plant of *Eucalyptus camaldulensis,* and the NAA concentrations used in the infection medium and sterilization medium, the precocious branches were infected with agrobacterium tumefaciens strain EHA101/pIG121-Hm in the same manner as described in Example 1 to produce transgenic calli. As a result, as shown in Table 2, transformation efficiency was high at 42% in the case the NAA concentration used in the infection medium and sterilization medium was 2mg/l as in Example 1, thereby increasing transformation efficiency 4 to 10 times more than transformation efficiency under other conditions.

TABLE 2

| Infection medium | | Sterilization medium | | Transformation efficiency (%) |
|---|---|---|---|---|
| NAA (mg/l) | 4-PU (mg/l) | NAA (mg/l) | 4-PU (mg/l) | |
| 2 | 0.2 | 2 | 0.2 | 42 |
| 2 | 0.2 | 0.02 | 0.2 | 11 |
| 0.02 | 0.2 | 2 | 0.2 | 4 |
| 0.02 | 0.2 | 0.02 | 0.2 | 14 |

Example 4

Test Plants

*Eucalyptus globulus* was used.

Preparation of Precocious Branches and Preparation of Agrobacterium tumefaciens

The procedures using Eucalyptus globulus were performed in the same manner as described in Example 1.

Infection of Eucalyptus globulus with Agrobacterium

Precocious branches of *Eucalyptus globulus* obtained in the same manner as described in Example 1 were transplanted to an infection induction medium containing 0.02 mg/l NAA, 1% sucrose and 0.2% gellan gum in B5 basal medium, and after culturing for 14 days under dark conditions, the infection-induction-treated precocious branches were removed and cut into segments measuring 2 to 10 mm with a knife. Moreover, a medium was prepared that contained 2 mg/l NAA, 0.2 mg/l 4-PU, 1 mM galactose, 10 μM acetosyringone and 3% sucrose in B5 basal medium, and the explant segments were soaked in an Agrobacterium tumefaciens strain LBA4404/pBI121 culture prepared in the same manner as described in Example 1. Next, the above explant segments were transplanted to an infection medium in the same manner as described in Example 1 and stationary cultured for 2 days at a temperature of 26° C. under dark conditions to infect with Agrobacterium tumefaciens.

Sterilization of Agrobacterium

The explant segments were transplanted to a sterilization medium containing 2 mg/l NAA, 0.2 mg/l 4-PU, 3% sucrose along with 250 mg/l of carbenicillin and 100 mg/l of vancomycin as antibiotics for sterilizing Agrobacterium attached to the explant segments. The explant segments were vertical-rotary-cultured for 7 days at a temperature of 26° C. and rotating speed of 2rpm under dark conditions to sterilized the Agrobacterium tumefaciens.

Formation of Transgenic Shoot Primordia

Explant segments completely sterilized of Agrobacterium tumefaciens were planted at the rate of 5 segments per test tube in a selection medium containing 0.02 mg/l IBA, 0.5 mg/l TDZ, 3% sucrose and 20 mg/l kanamycin in B5 basal medium. As a result of vertical-rotary-culturing at a rotating speed of 2 rpm and temperature of 26° C. for 7 days under dark conditions and then for 1 month under illumination at a illumination intensity of 2,000 lux at the lower limit and 20,000 lux at the upper limit. The formation of transgenic calli that were yellowish-white and measured 2 to 3 mm was observed on the explant segments. Culturing of the resulting calli was continued by subculturing into fresh medium at intervals of 14 to 40 days. Transgenic shoot primordia were obtained at 40 to 120 days from the start of vertical-rotary-culturing under illumination.

Regeneration of Transgenic Plants

Shoot primordia cut into squares measuring about 5 mm on a side were transplanted to a seedling medium containing 0.3 mg/l BA, 1 μM, 2,3,5-triiodobenzoic acid (TIBA), 1% sucrose, 0.2% gellan gum and 20 mg/l kanamycin in B5 basal medium to regenerate shoots from transgenic shoot primordia obtained by rotary culturing. As a result of culturing for 16 hours under illumination at 26° C. and illumination intensity of 4,000 lux, shoot regeneration was observed 1 month after the start of the culturing. By transplanting the resulting shoots in a rooting medium containing 0.1 mg/l IBA, 1% sucrose, 0.1% polyvinylpyrrolidone, 0.15% gellan gum and 20 mg/l kanamycin in B5 basal medium, complete plants were grown, wherein rooting was observed after 1 month.

Confirmation of Presence and Expression of Transgene in Transgenic Plants

The presence of the transgene was confirmed by PCR for the plants obtained by transformation in the same manner as Example 1. In addition, the expression of GUS gene was confirmed by tissue staining.

Example 5

Precocious shoot induction, infection induction, Agrobacterium infection, sterilization, shoot primordia formation and regeneration were able to be carried out efficiently according to the same method as described in Example 1 using *Eucalyptus grandis.*

Example 6

Precocious shoot induction, infection induction, Agrobacterium infection, sterilization, shoot primordia formation and regeneration were able to be carried out efficiently according to the same method as described in Example 1 using a hybrid of *Eucalyptus grandis* x *Eucalyptus urophylla*.

Effect of the Invention

According to the present invention, stable transgenic plants were able to be produced both efficiently and in a short period of time even from mature trees of outdoor Eucalyptus plants for which production of transgenic plants were heretofore difficult. Thus, since useful genes can be inserted into plus trees produced by conventional breeding methods of selection and hybridization, it is possible to provide a stable supply of new varieties in a shorter period of time than in the prior art while also retaining useful transformation that exceeds the biological species.

What is claimed is:

1. A process for production of transgenic Eucalyptus plants from a mature tree of Eucalyptus plant, comprising the steps of:

(1) preparing a shoot tip explant from a mature tree of Eucalyptus plant;

(2) inducing the shoot tip explant to form adventitious shoots;

(3) pre-culturing the adventitious shoots to prepare infection in an infection induction medium;

(4) infecting segments of explant cut out from the pre-cultured adventitious shoots, with Agrobacterium tumefaciens in an infection medium;

(5) rotary-culturing the segments of the explant from the step (4) in a medium for sterilization containing antibiotics so as to sterilize the Agrobacterium tumefaciens attached to the segments of the explant, to form calli and to select transformed calli;

(6) forming shoot primordia from the transformed calli; and (7) regenerating transgenic plants from the transformed shoot primordia.

2. A process according to claim 1, wherein the adventitious shoots are precocious branches or axillary shoots.

3. A process according to claim 2, wherein the adventitious shoots are precocious branches.

4. A process according to claim 1, wherein the pre-culturing in the step (3) is carried out in an infection induction medium containing naphthaleneacetic acid for 7 to 14 days under the dark condition.

5. A process according to claim 1 wherein the Eucalyptus plant is selected from the group consisting of *Eucalyptus camaldulensis, Eucalyptus globulus, Eucalyptus grandis, Eucalyptus urophylla* and a hybrid of one of said species as the maternal or paternal tree.

* * * * *